(12) United States Patent
Kilbey

(10) Patent No.: US 9,750,630 B2
(45) Date of Patent: Sep. 5, 2017

(54) PNEUMATIC KNEE BRACE WITH REMOVABLE STAYS

(71) Applicant: Brian E Kilbey, DeFuniak Springs, FL (US)

(72) Inventor: Brian E Kilbey, DeFuniak Springs, FL (US)

( * ) Notice: Subject to any disclaimer, the term of this patent is extended or adjusted under 35 U.S.C. 154(b) by 825 days.

(21) Appl. No.: 13/874,620

(22) Filed: May 1, 2013

(65) Prior Publication Data

US 2014/0330184 A1 Nov. 6, 2014

(51) Int. Cl.
*A61F 5/01* (2006.01)
*A61F 7/00* (2006.01)

(52) U.S. Cl.
CPC .......... *A61F 5/0123* (2013.01); *A61F 5/012* (2013.01); *A61F 5/0106* (2013.01); *A61F 5/0109* (2013.01); *A61F 2007/0039* (2013.01); *A61F 2007/0042* (2013.01)

(58) Field of Classification Search
CPC .. A61F 5/00; A61F 5/01; A61F 5/0102; A61F 5/012; A61F 5/0123; A61F 5/0125; A61F 5/37; A61F 7/00; A61F 2007/0001; A61F 2007/0039; A61F 2007/0042; A61F 7/0085; A61F 5/0106; A61F 5/0109
USPC .... 128/846, 869, 878, 881, 882; 602/5–6, 9, 602/12, 14, 16, 20, 23, 26, 60–63, 75, 78, 602/13
See application file for complete search history.

(56) References Cited

U.S. PATENT DOCUMENTS

| | | | | |
|---|---|---|---|---|
| 4,366,813 A * | 1/1983 | Nelson | ................. | A61F 5/0109 2/24 |
| 4,986,263 A * | 1/1991 | Dickerson | ............ | A61F 5/0109 2/22 |
| 5,261,871 A * | 11/1993 | Greenfield | ........... | A61F 5/0109 602/19 |
| 5,395,307 A * | 3/1995 | Fan | ...................... | A61F 13/148 128/DIG. 15 |
| 5,407,421 A * | 4/1995 | Goldsmith | ............ | A61F 5/012 128/882 |
| 5,451,201 A * | 9/1995 | Prengler | ................ | A61F 5/012 602/13 |
| 5,513,658 A * | 5/1996 | Goseki | ................. | A61F 5/0109 128/882 |
| 5,588,956 A * | 12/1996 | Billotti | .................... | A61F 5/012 128/DIG. 20 |
| 5,656,023 A * | 8/1997 | Caprio, Jr. | ........... | A61F 5/0106 602/26 |

(Continued)

*Primary Examiner* — Keri J Nelson
(74) *Attorney, Agent, or Firm* — J. Wiley Horton

(57) ABSTRACT

A reconfigurable knee brace which is particularly suitable for cold therapy. The brace includes a large wrap which fits over the front of the leg and wraps around the knee. Two or more securing straps are provided to hold the wrap in place. Once in position, an internal air bladder can be inflated to secure the fit. The user inflates the air bladder using an included squeeze pump and selectively deflates the bladder using a release button. One or more removable stays are positioned on the left and right lateral sides of the knee. When the stays are in position, the knee is held in place and cannot flex or extend. However, the stays are made removable. Once the stays are removed, the knee is able to flex and extend (though it is still stabilized by the encircling wrap).

13 Claims, 17 Drawing Sheets

(56) References Cited

U.S. PATENT DOCUMENTS

| | | | | |
|---|---|---|---|---|
| 5,743,867 A * | 4/1998 | Hickling | A61F 7/02 | |
| | | | 602/2 | |
| 5,792,084 A * | 8/1998 | Wilson | A61F 5/012 | |
| | | | 602/13 | |
| 5,993,405 A * | 11/1999 | Wynn | A61F 5/05841 | |
| | | | 602/26 | |
| 6,109,267 A * | 8/2000 | Shaw | A61F 5/0104 | |
| | | | 128/882 | |
| 6,110,135 A * | 8/2000 | Madow | A61F 5/0106 | |
| | | | 128/892 | |
| 6,464,658 B1 * | 10/2002 | Darcey | A61F 5/05825 | |
| | | | 602/23 | |
| 6,773,411 B1 * | 8/2004 | Alvarez | A61F 5/0109 | |
| | | | 602/27 | |
| 7,615,019 B2 * | 11/2009 | Nordt, III | A41D 13/05 | |
| | | | 602/16 | |
| 7,862,529 B2 * | 1/2011 | Brown | A61F 5/0106 | |
| | | | 128/882 | |
| 8,025,632 B2 * | 9/2011 | Einarsson | A41D 13/1281 | |
| | | | 602/23 | |
| 2010/0285938 A1 * | 11/2010 | Latronica | A63B 21/16 | |
| | | | 482/124 | |

* cited by examiner

PNEUMATIC KNEE BRACE WITH REMOVABLE STAYS

CROSS-REFERENCES TO RELATED APPLICATIONS

This application is a non-provisional application claiming priority to U.S. Provisional Application No. 61/640,912 filed on May 1, 2012.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to the field of medical products. More specifically, the invention comprises a knee brace which is configurable to allow or restrict flexion of the knee while applying cold therapy.

2. Description of the Related Art

Knee surgeries are now commonly performed using minimally invasive techniques. Most surgeons prefer to begin moving the knee joint very shortly after surgery. It is also preferable to provide cold therapy to minimize swelling. Cold therapy assumes a variety of forms—ranging from simple ice or gel packs to sophisticated chilled water circulating devices. These devices must provide sufficient cooling to minimize swelling yet not cool the tissue to the point where damage might occur.

Initial motion of the knee joint is often performed by placing the knee in a passive range of motion ("passive ROM") machine. This device moves the joint through a defined range without actually employing the knee structures to produce the motion. It is common to alternate between periods of cold therapy and passive ROM therapy.

A wrap is typically used to hold the cold therapy components in position. This wrap often is configured to immobilize the knee so that the patient cannot accidentally introduce unwanted motion. When passive ROM therapy is again desired, the immobilizing wrap is removed and the patient is placed in the passive ROM machine. A separate passive ROM brace may be applied in some cases. In any event, the wrap used for the cold therapy must be removed in order to perform the passive ROM. This fact means that the benefit of cold therapy is lost during the passive ROM.

It would be advantageous to provide a knee brace which could immobilize the knee, but which could also be reconfigured to permit flexion and extension when desired. It would also be advantageous for such a brace to include cold therapy features. The present invention proposes such a brace.

BRIEF SUMMARY OF THE PRESENT INVENTION

The present invention comprises a reconfigurable knee brace which is particularly suitable for cold therapy. The brace includes a large wrap which fits over the front of the leg and wraps around the knee. Two or more securing straps are provided to hold the wrap in place. Once in position, an internal air bladder can be inflated to secure the fit. The user inflates the air bladder using an included squeeze pump and selectively deflates the bladder using a release button.

One or more removable stays are positioned on the left and right lateral sides of the knee. When the stays are in position, the knee is held in place and cannot flex or extend. However, the stays are made removable. Once the stays are removed, the knee is able to flex and extend (though it is still stabilized by the encircling wrap).

The inner facing surface of the wrap is provided with attachment features which allow cold therapy bags to be positioned and held in place. The cold therapy bags preferably include a substance which transitions from a solid to a liquid in order to utilize the heal transfer advantages of a phase change.

The removable stays are placed in the brace during periods of rest and removed when motion is desired. The cold therapy bags preferably remain in place in all configurations of the brace. This feature allows the cold therapy to continue while passive range of motion therapy is conducted.

The brace preferably includes a removable anterior brace. This device provides additional rigidity to the brace during periods of rest. It may be easily removed when motion of the knee is desired.

Figure 1:
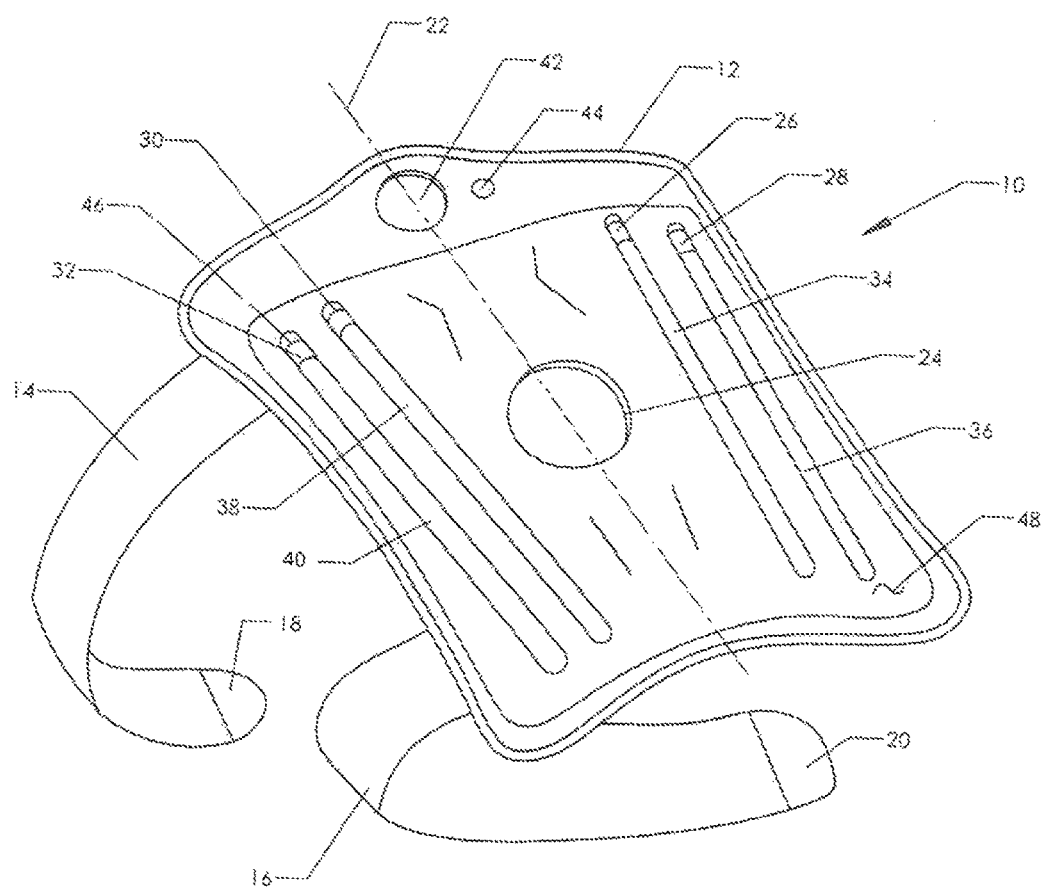
FIG. 1 is a perspective view, showing the outward facing surfaces of the knee brace.

| REFERENCE NUMERALS IN THE DRAWINGS | | | |
|---|---|---|---|
| 10 | knee brace | 12 | wrap |
| 14 | top strap | 16 | bottom strap |
| 18 | hook panel | 20 | hook panel |
| 22 | anterior medial axis | 24 | knee cap relief |
| 26 | first left lateral stay | 28 | second left lateral stay |
| 30 | first right lateral stay | 32 | second right lateral stay |
| 34 | stay pocket | 36 | stay pocket |
| 38 | stay pocket | 40 | stay pocket |
| 42 | squeeze pump | 44 | release |
| 46 | pocket opening | 48 | loop covering |
| 50 | edge band | 52 | staked seam |
| 54 | inner panel | 56 | outer panel |
| 58 | air bladder | 60 | cold pack |
| 62 | knee cap relief | 64 | hook panel |
| 66 | cooling medium | 68 | friction strip |
| 70 | leg | 72 | knee cap |
| 74 | posterior brace | 76 | reinforced pad |
| 78 | left lower pad strap | 80 | right lower pad strap |
| 82 | left upper pad strap | 84 | right upper pad strap |
| 86 | hook pad | 88 | hook pad |
| 90 | hook pad | 92 | hook pad |
| 94 | anchor | 96 | hook panel |
| 98 | loop | 100 | loop |
| 102 | strap | | |

DETAILED DESCRIPTION OF THE INVENTION

While the invention has several important components which will be found in all embodiments, it may be constructed in many different ways. Thus, the following descriptions and accompanying illustrations should properly be viewed as providing exemplary embodiments and should not be viewed as limiting.

FIG. 1 shows knee brace 10, which includes wrap 12 and appropriate features for securing the wrap to a patient's knee. The wrap has an outward facing surface and an inward facing surface. The outward facing surface is shown. A portion of the outward facing surface is preferably provided with loop covering 48 (VELCRO material).

In the embodiment shown bottom strap 16 and top strap 14 are used to secure the wrap. Top strap 14 has hook panel 18 while bottom strap 16 has hook panel 20. The two straps are wrapped around the patient's leg and they are secured to the wrap by pressing the respective hook panels into loop covering 48 on the exterior surface of the wrap. The straps are thereby made infinitely adjustable.

Wrap 12 has anterior medial axis 22. Knee cap relief 24 is located along this axis. The knee cap relief allows the patient's knee cap to extend through the knee brace. Removable lateral stays are provided on both sides of anterior medial axis 22. Stay pocket 34 and stay pocket 36 are provided on the left side of the anterior medial axis (The directional term "left" is from the vantage point of a patient wearing the brace). Stay pocket 38 and stay pocket 40 are provided on the right side of the anterior medial axis.

Each stay provides a sliding fit for a removable stay. The removable stays are typically long pieces of aluminum. First left lateral stay 26 slides into stay pocket 34. Second left lateral stay slides into stay pocket 36. First right lateral stay 30 slides into stay pocket 38. Second right lateral stay 32 slides into stay pocket 40. Each stay pocket includes a pocket opening 46. The stay pockets are preferably made of elastic material so that they frictionally engage and hold the stays in place.

The wrap includes an inflatable air bladder which allows the user to adjust the amount of compression provided by the knee brace. In the embodiment shown, the air bladder is inflated by squeezing squeeze pump 42 (a type of hand pump). Squeezing squeeze pump 42 inflates the air bladder. Pressing release 44 deflates the air bladder. Thus, the patient has manual control of the inflation and deflation of the air bladder.

Figure 2:
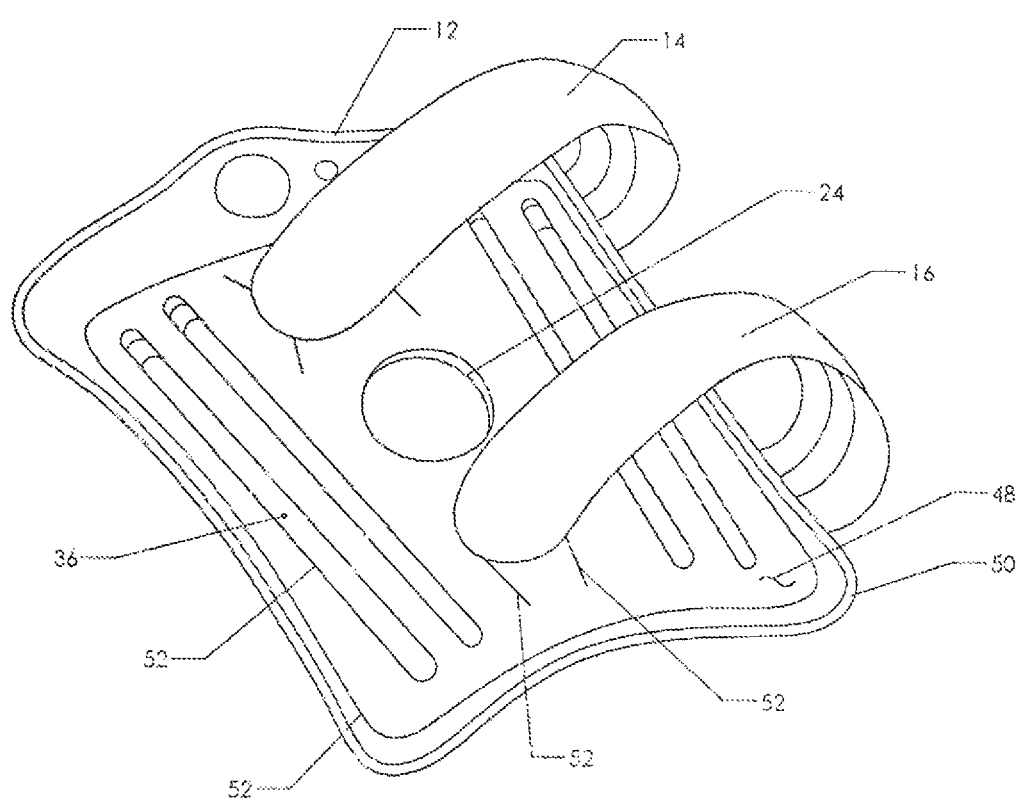
FIG. 2 is a perspective view, showing the inward facing surfaces of the knee brace.

FIG. 2 shows wrap 12 from the opposite side (the inward facing side). The inward facing side also preferably includes loop covering 48 over at least a portion of its area. Edge band 50 is provided around the perimeter to prevent tearing or fraying of the material.

Figure 3:
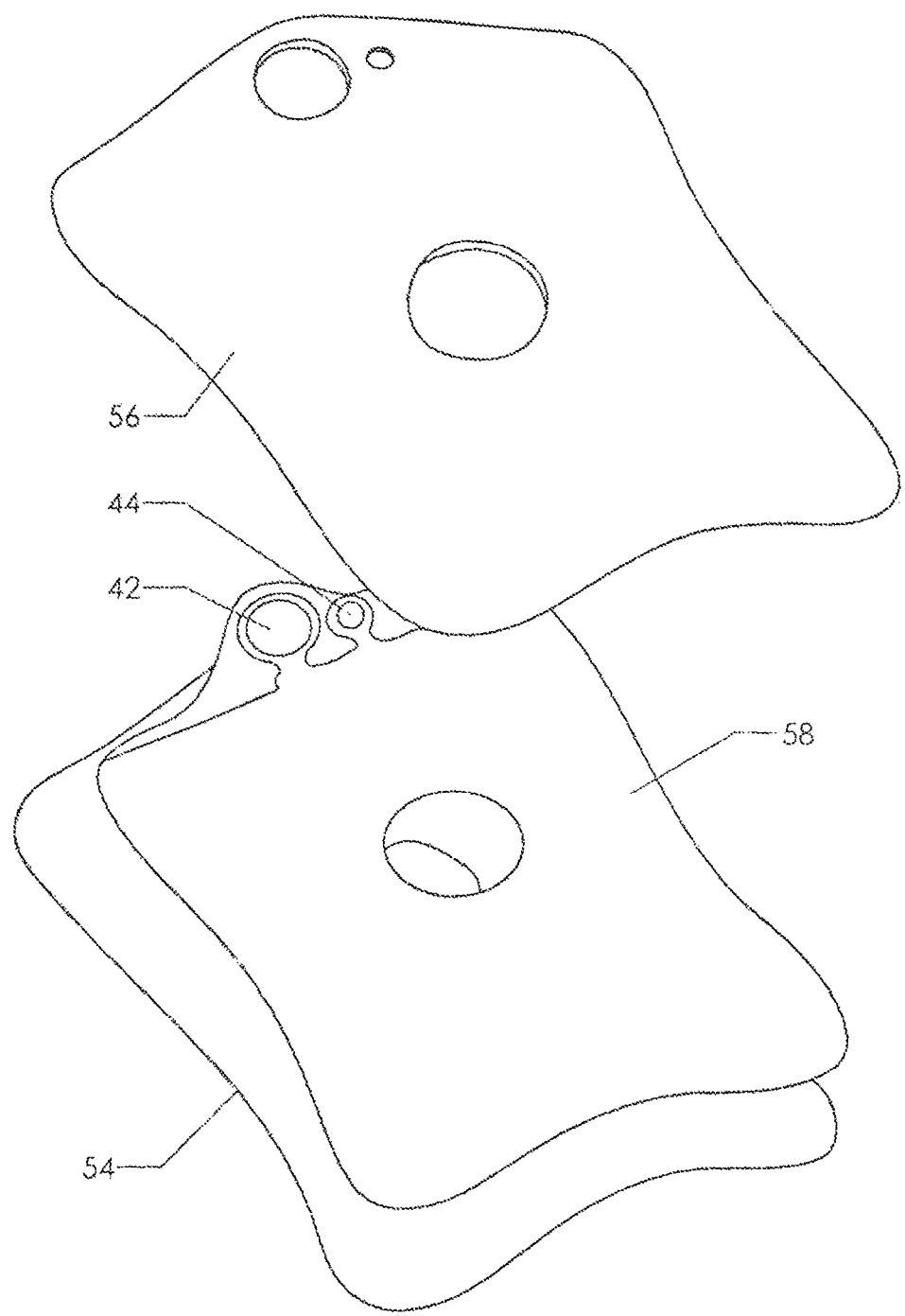
FIG. 3 is an exploded perspective view, showing the layered construction of the brace, including the internal air bladder.

Turning now to FIG. 3 the construction of the wrap will be discussed. One method of constructing the wrap is to "sandwich" air bladder 58 between outer panel 56 and inner panel 54. The air bladder actually includes two layers joined along the edges to form an inflatable cavity. Squeeze pump 42 and release 44 are connected to this internal cavity using appropriate check valves so that squeezing the pump inflates the cavity and pressing the release deflates it. Such valves and connections are well known in the art and they have therefore not been described in detail.

One could join the assembly of FIG. 3 by connecting the layers only along the edges. However, if this method is used, inflating air bladder 53 will cause the middle to expand more than the edges—producing uneven pressure. It would therefore be better to join all the layers (including both layers of the air bladder) together at various intermediate positions. This is analogous to the creation of longitudinal seams in an air mattress. The seams segregate the air mattress into long parallel chambers.

An analogous technique can be used to join the assembly of FIG. 3. All the layers are joined by "staking" them together. The staking can be done by pressing the layers together and melting them along a specified seam ("heat staking"). Other joining techniques could be used as well. The two straps 14 and 16 are joined to the wrap—typically by sewing.

Returning to FIG. 2, the reader will note the creation of various staked seams 52. All the layers are joined together at each staked seam. One staked seam extends around the wrap's perimeter. Others follow the outlines of the stay pockets 36. Still more are relatively short seams near the center of the wrap (to prevent uneven extension of the air bladder). Still another seam extends around the perimeter of the knee relief hole. None of the staked seams extend completely across the air bladder. Thus, although the air bladder is divided into individual chambers all the chambers are connected and the pressure therein will remain uniform.

Figure 4:
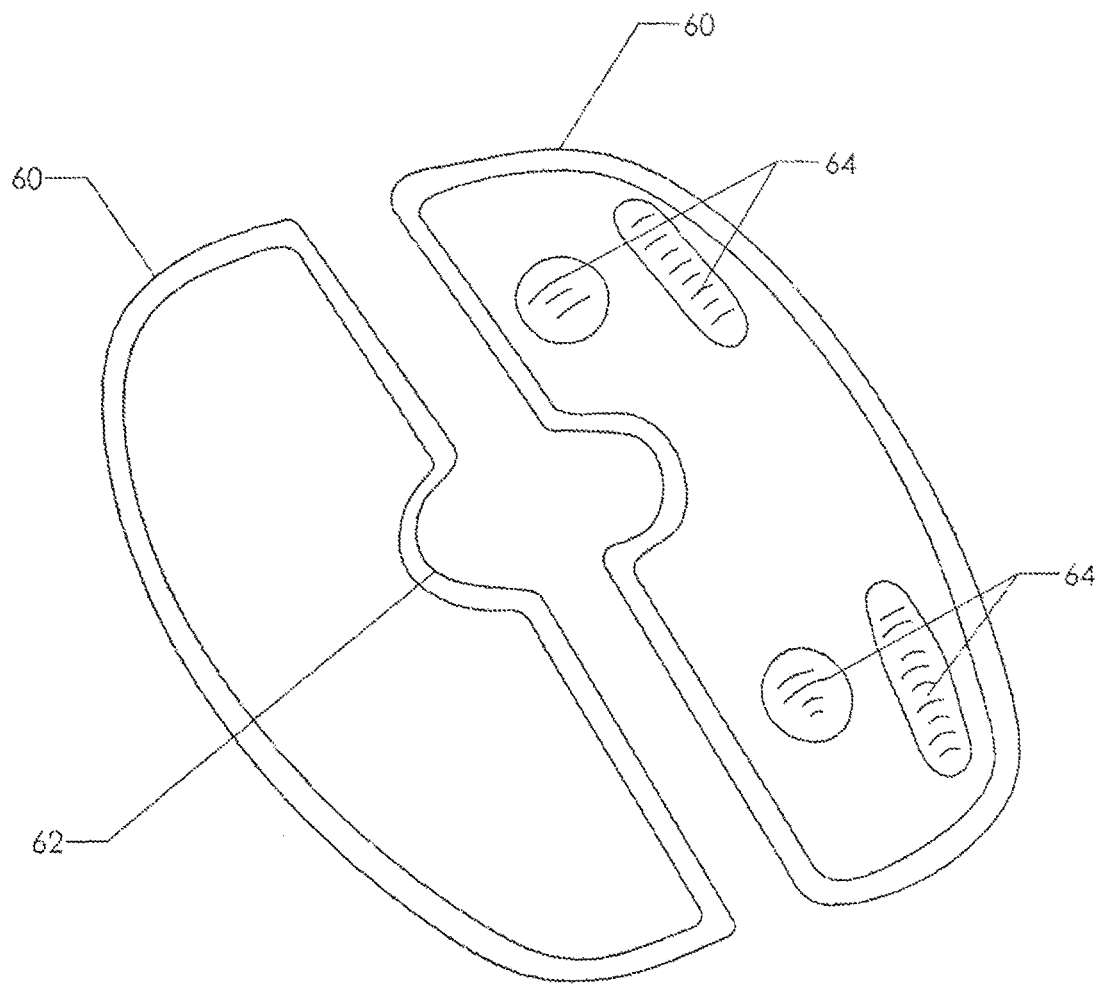
FIG. 4 is a perspective view, showing a pair of cold packs configured for use with the knee brace.

One of the main objectives of the present invention is to effectively administer cold therapy. FIG. 4 shows a pair of cold packs 60 used for this purpose. Each cold pack 60 is made of two impermeable layers sealed along their perimeters. The cooling medium is contained within the sealed interior of each cold pack.

The shape of the cold packs shown in FIG. 4 is configured to fit inside wrap 12. Thus, a knee cap relief 62 is provided on each cold pack. The left cold pack 60 in the view of FIG. 4 is facing toward the surface it will be applied to (the inward facing surface of the wrap) while the right cold pack 60 is turned upside down in order to show the attachment features. The reader will observe that one or more hook panels 64 are provided on the surface which normally faces the inside of the wrap.

Figure 6:
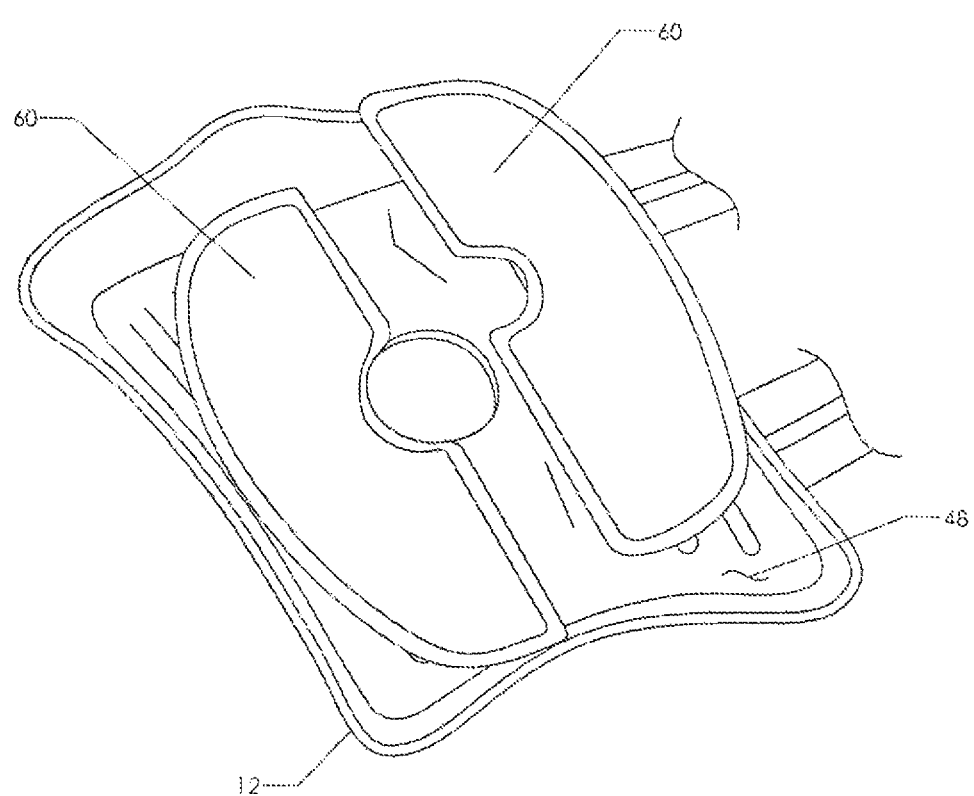
FIG. 6 is an exploded perspective view, showing the application of a pair of cold packs to the knee brace.

FIG. 6 shows two cold packs 60 in position to be attached to the inward facing surface of wrap 12. The hook panels on each of the cold packs (facing away from the viewer) are pressed against loop covering 48 to hold the pack in place.

This system allows the packs to be easily replaced. Each pack of course has a limited heat absorption capacity and when this is exhausted it must be replaced by a fresh pack.

Figure 5:
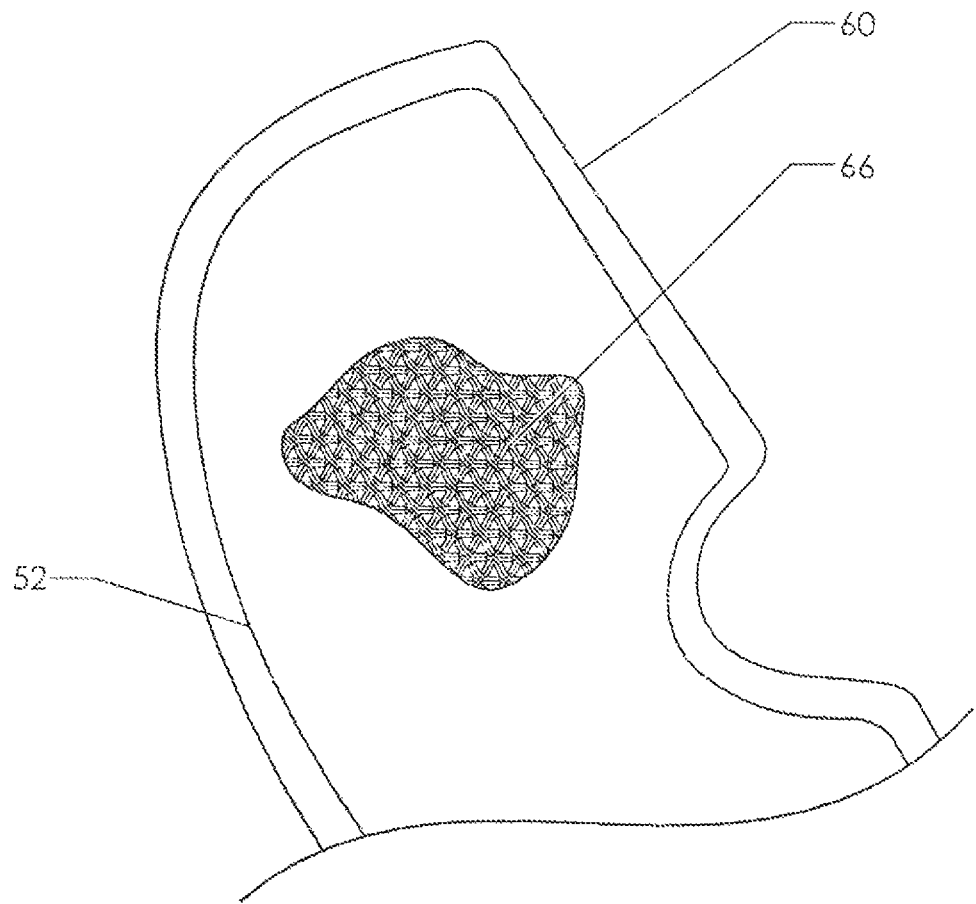
FIG. 5 is a detail view with a cutaway, showing the preferred cooling medium in the cold packs.

FIG. 5 shows a cutaway with the preferred cooling medium 66. The preferred cooling medium is one that freezes between about 5 degrees Celsius and about 20 degrees Celsius. Such a medium can absorb considerable heat via the phase change from a solid to a liquid. In addition, such a cooling medium poses little risk of tissue damage (as it will remain at its melting temperature until all the medium has transitioned from a solid to a liquid).

Figure 7:
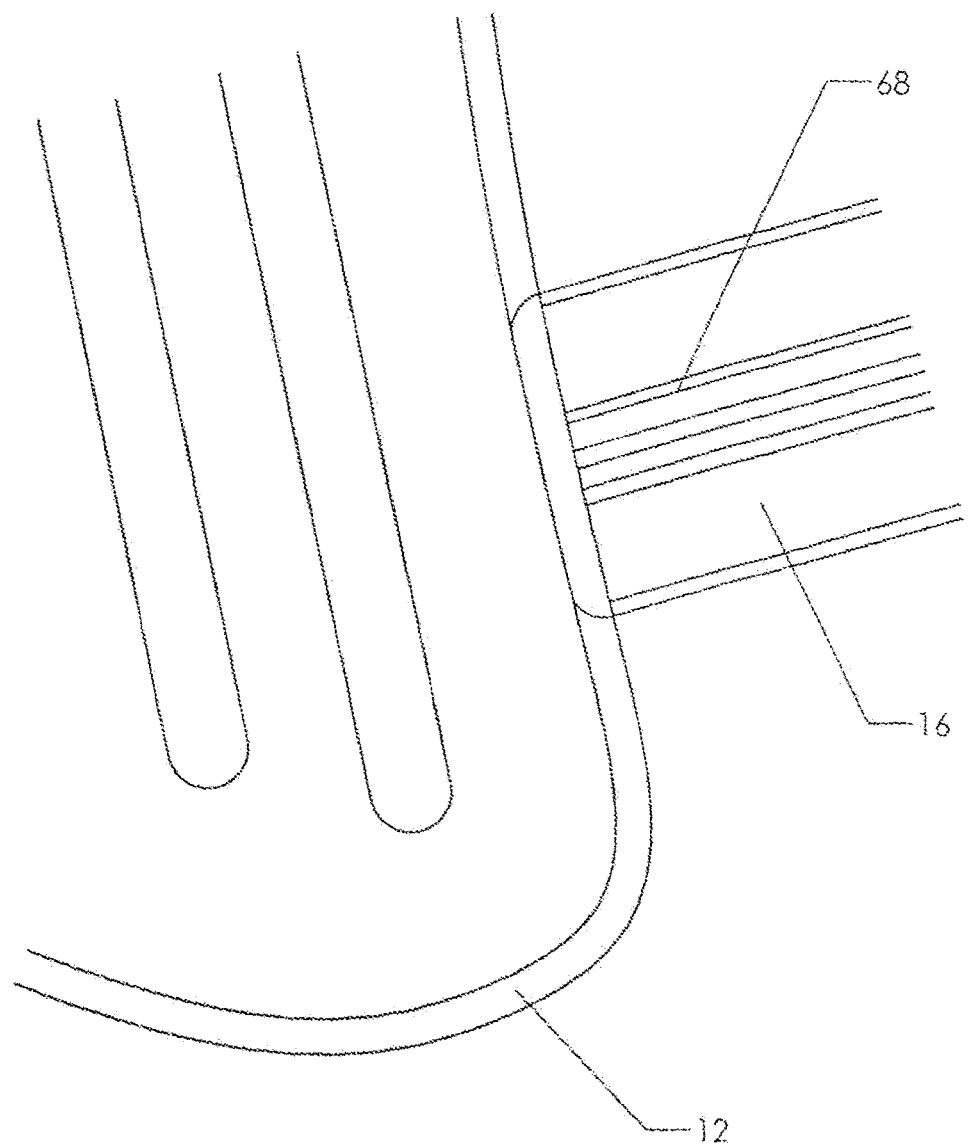
FIG. 7 is a detail view, showing the inclusion of a friction strip on a securing strap.

Returning now to FIG. 6, the reader will appreciate that once the cold packs are attached to wrap 12, wrap 12 is placed around the patient's knee. It is important that the wrap remain in the correct position. FIG. 7 shows a detail view of the inward facing surface of bottom strap 16. This preferably includes a friction enhancing feature such as friction strip 68. Friction strip 68 is one or more bands of a substance having a high coefficient of friction. These bear against the patient's skin so the material should also be comfortable to the patient. The friction strips help to hold the wrap in the proper position with respect to the patient's anatomy. These are particularly important when the knee is flexed during passive ROM therapy.

Figure 17:
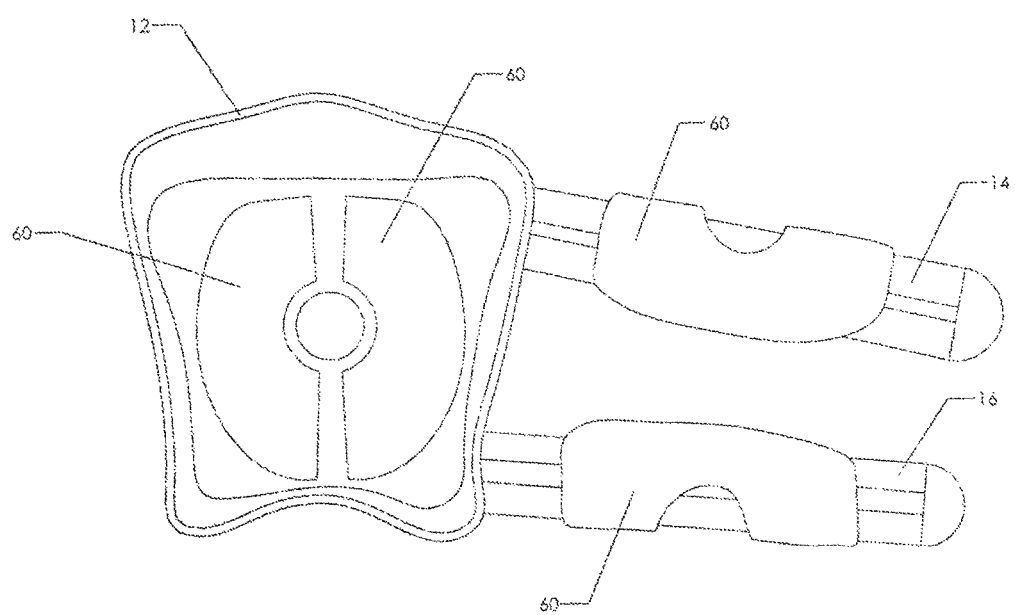
FIG. 17 shows a plan view of the inward facing side of the knee brace, with the addition of cold packs to the top and bottom straps.

It may also be desirable to apply cold packs to the posterior portion of the knee. FIG. 17 shows the inward facing surface of wrap 12 with two cold packs 60 applied to the wrap itself. The reader will recall that the surfaces of top strap 14 and bottom strap 16 which face the viewer in FIG. 17 are preferably also covered in loop material. Additional cold packs 60 may therefore be placed on the straps themselves. These cold packs may be positioned in a position which causes them to be aligned with the posterior axis of the knee joint when the brace is installed.

Figure 8:
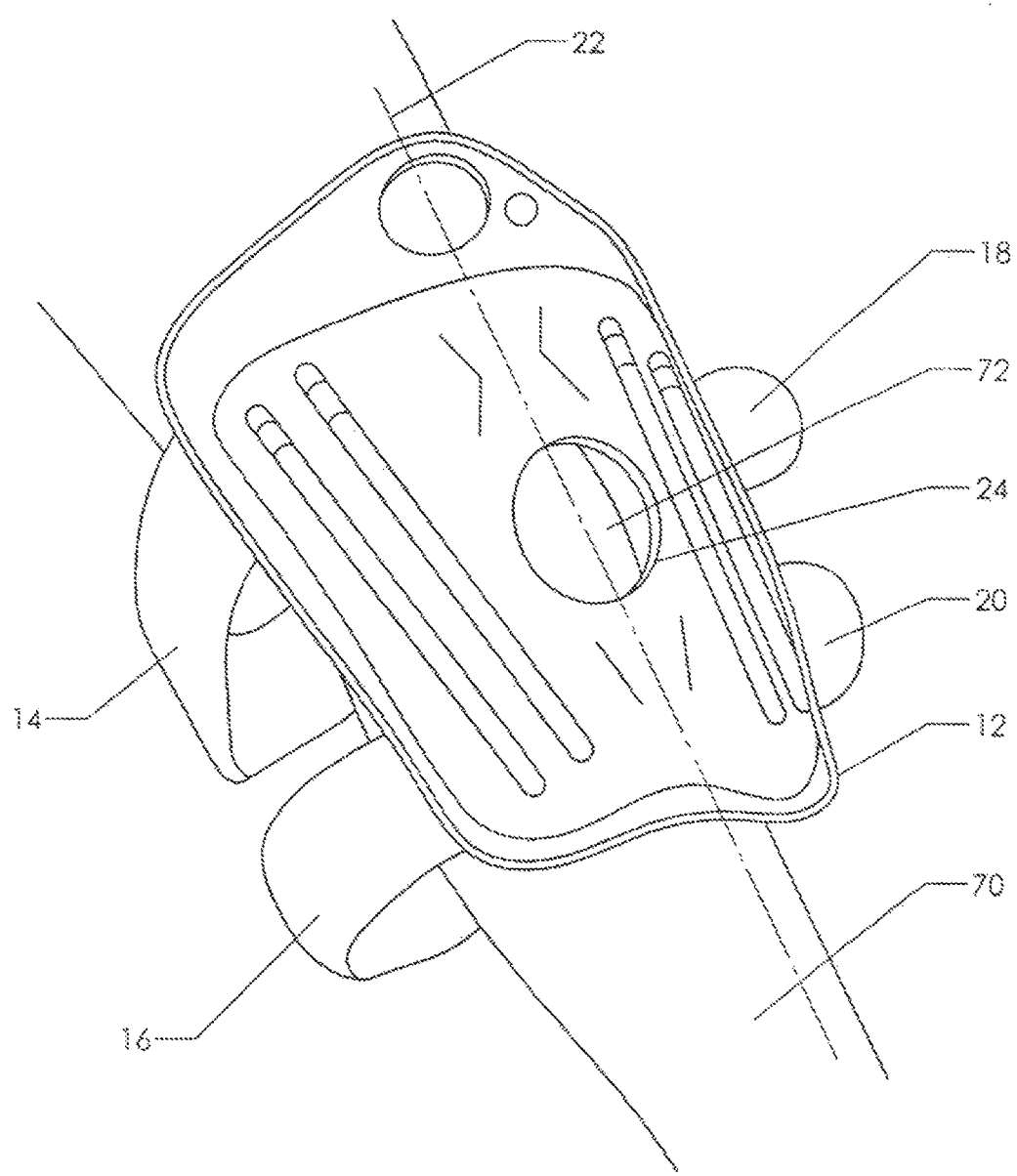
FIG. 8 is a perspective view, showing the knee brace being installed on a patient's knee.
Figure 9:
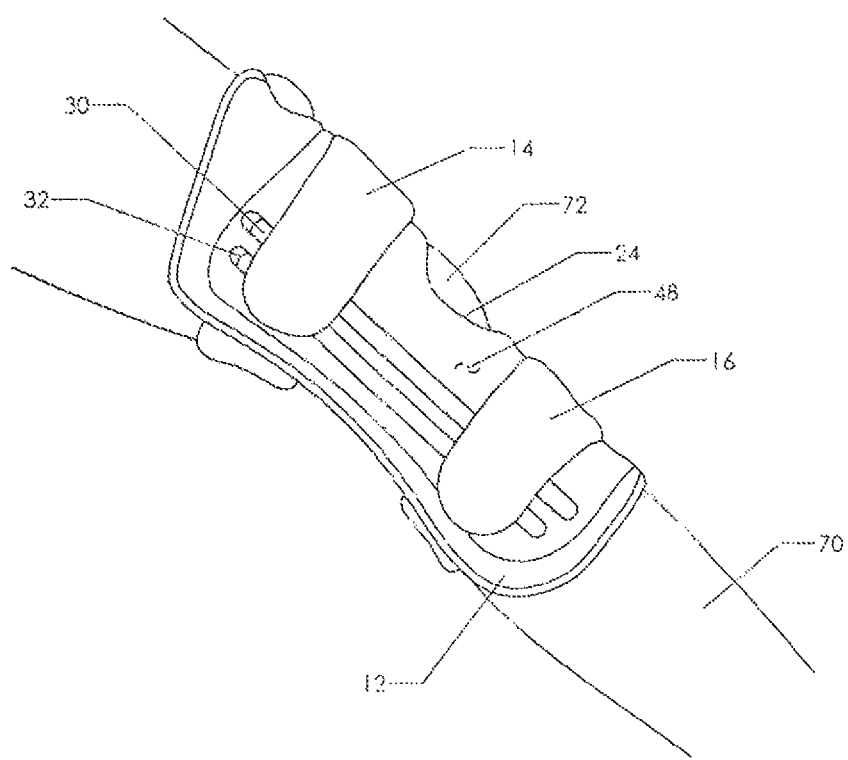
FIG. 9 is a side elevation view of the knee brace installed on a patient's knee.

FIGS. 8 and 9 show the knee brace being installed on a patient. In FIG. 8, wrap 12 is placed over the anterior portion of leg 70, with kneecap relief 24 being aligned with knee cap 72. Anterior medial axis 22 is aligned with the centerline of the leg. Top strap 14 and bottom strap 16 are passed around the leg and drawn tight. Hook panels 18 and 20 are then pressed against the outward facing surface of the wrap, where they engage the loop covering and are thereby secured.

FIG. 9 shows a side elevation view of the installed brace. The reader will observe that top strap 14 and bottom strap 16 have been tightened appropriately. The top and bottom straps are preferably made of elastic material so they may be stretched as desired. The hook panels on the two straps may be secured to loop covering 48 in any suitable position. This fact allows the knee brace to be secured over the leg with the anterior medial axis in proper alignment.

The lateral stays are placed along the right and left lateral sides of the knee. In the view of FIG. 9, first right lateral stay 30 and second right lateral stay 32 are properly positioned. When these lateral stays are in place (along with the lateral stays on the opposite side of the brace) flexion of the knee is greatly inhibited. The knee will be held in the position shown.

The user can pump the squeeze pump to inflate the internal air bladder and thereby press the cold packs firmly around the knee joint. The user is given control of the amount of pressure desired. Once the knee brace is properly secured as shown, pumping the squeeze pump will increase the pressure and conform the cold packs to the varying geometry of the knee. The cold therapy is thereby optimized.

Figure 10:
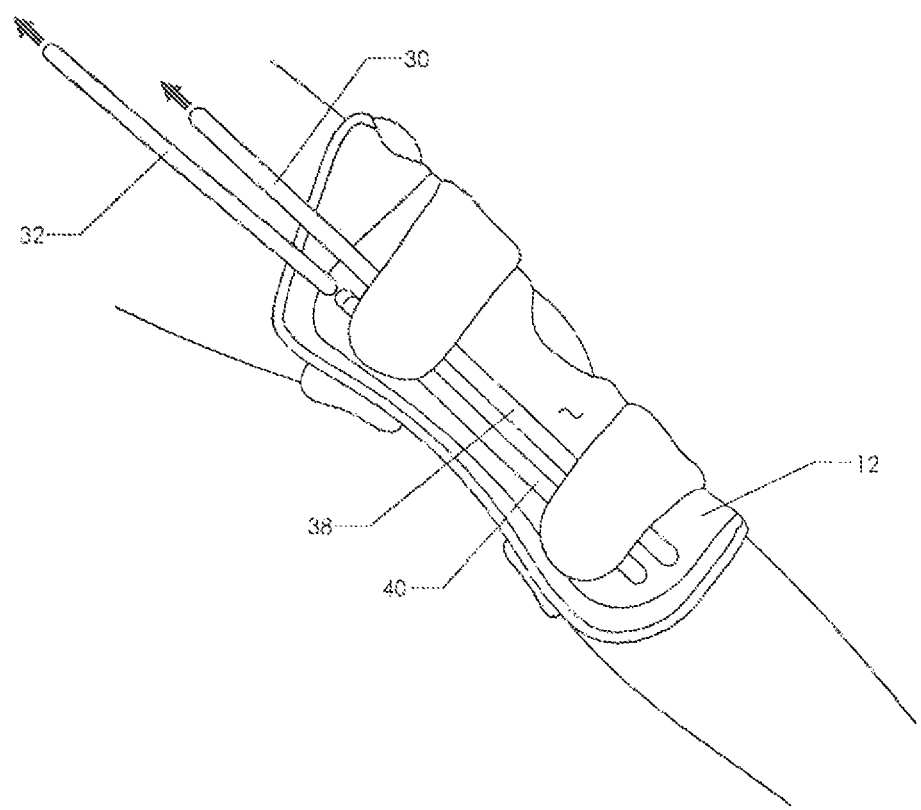
FIG. 10 is a side elevation view, showing the removal of the lateral stays.

As mentioned initially, many surgeons order passive ROM therapy very shortly after the surgery is completed. It is conventional to remove the knee brace and cold therapy devices in order to perform passive ROM. However, with the present invention, removal of the brace is not necessary. FIG. 10 illustrates how the lateral stays can be removed without removing the brace. First right lateral stay 30 and second right lateral stay 32 may both be pulled out of the respective stay pockets as indicated by the arrows. The same may be done for the stays on the far side.

Figure 11:
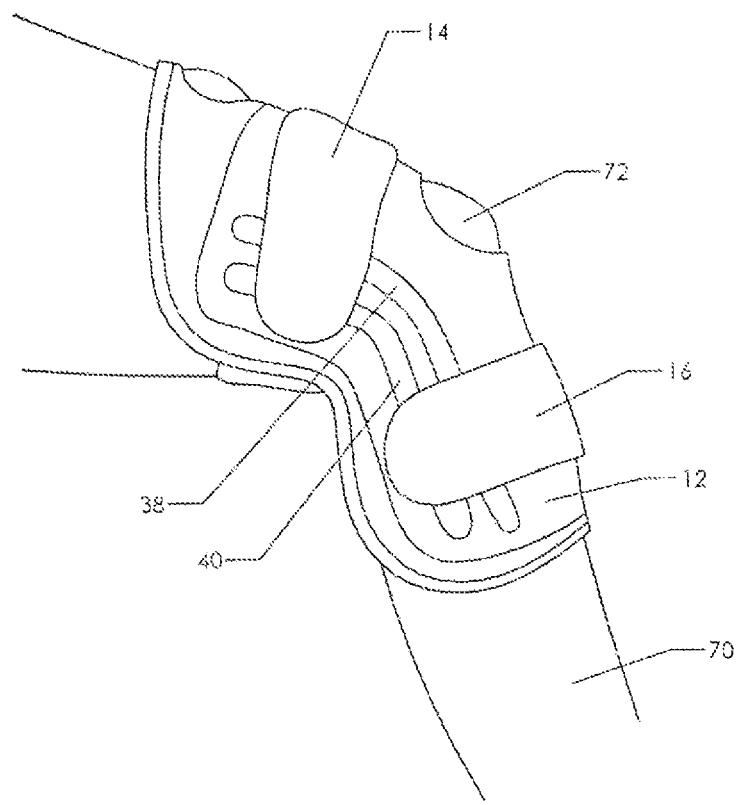
FIG. 11 is a side elevation view, showing the flexion of the knee and the brace when the lateral stays are removed.

FIG. 11 shows the brace with the lateral stays removed. In this second configuration the knee may be flexed through nearly its full range of motion. This flexion may also occur with the cold packs remaining in position. Thus, the knee may be placed in a passive ROM machine with the brace in place and with the cold therapy continuing throughout the passive ROM therapy. The user may wish to partially or completely deflate the air bladder during the motion therapy, but this is of course easily done using the release button.

Figure 12:
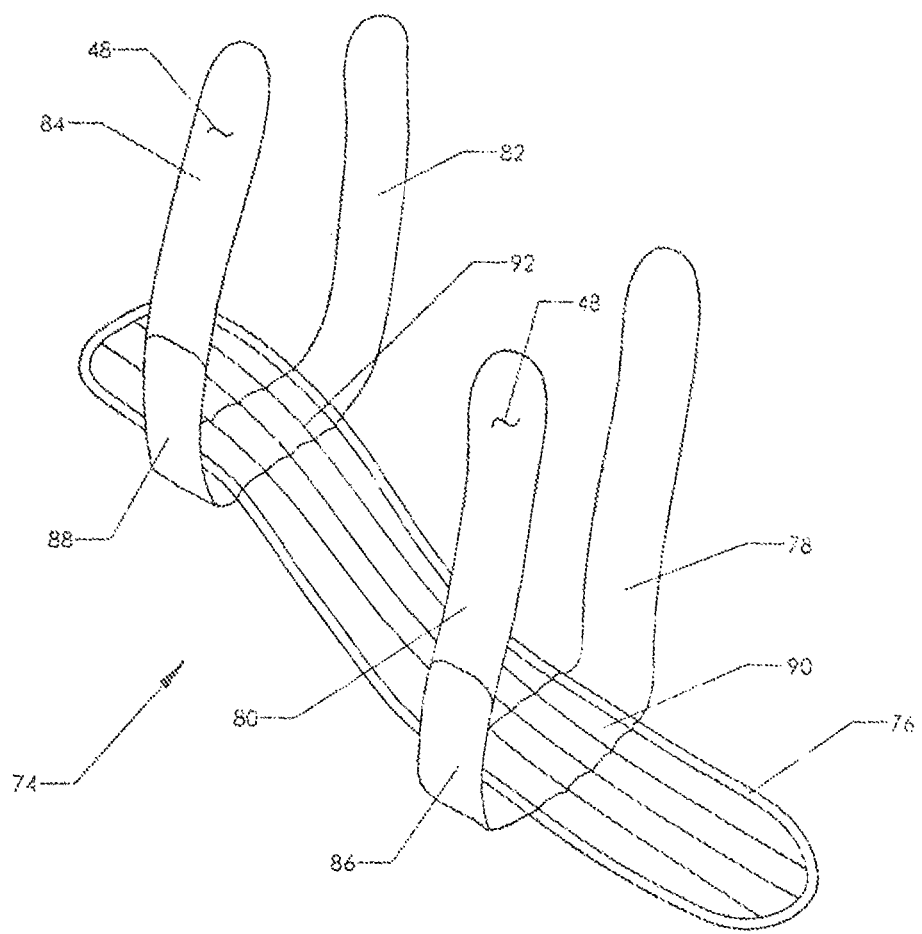
FIG. 12 is a perspective view, showing a removable anterior brace.

In some instances it may be desirable to provide additional stability to the knee joint. It is therefore preferable to provide a supplemental bracing element. FIG. 12 shows this element—which is designated as posterior brace 74. Reinforced pad 76 includes one or more stays within a cover. The stays are preferably long and thin aluminum bars which may be bent and shaped to suit the particular patient's anatomy. Four straps are provided to secure the posterior brace in position. These are left lower pad strap 78, right lower pad strap 80, left upper pad strap 82, and right upper pad strap 84. Each strap is preferably also provided with a hook pad—such as hook pad 86 and hook pad 88. In addition, reinforced pad 76 is also provided with a hook pad 90 and a hook pad 92. Hook pad 90 and hook pad 92 are used to secure anterior brace 74 to top strap 14 and bottom strap 16—as will be explained, subsequently.

Figure 13:
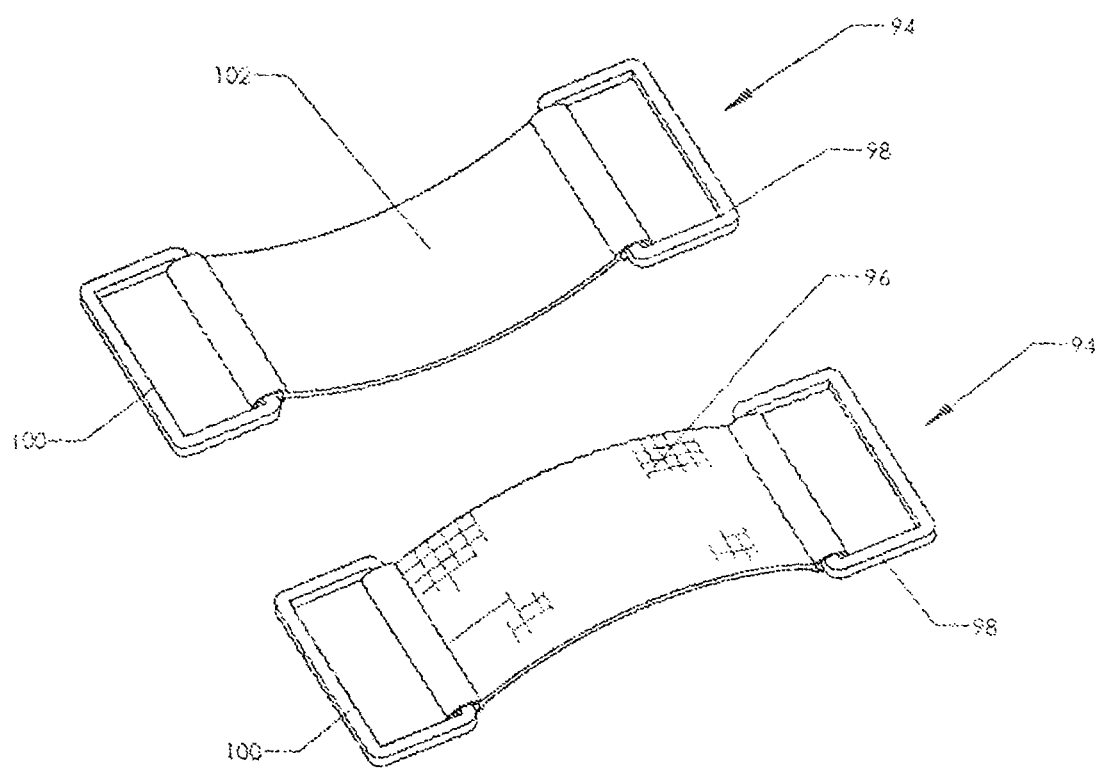
FIG. 13 is a perspective view, showing two anchors.

Another securing component is useful for attaching the posterior brace. FIG. 13 shows this component—which is designated as anchor 94. FIG. 13 shows two such anchors, with the upper example being in the orientation in which it is commonly used and the lower example being inverted. Each anchor 94 has a strap 102 with a loop 98 on either end. The side of the strap which ordinarily faces the outward facing surface of the knee brace includes a hook panel 96.

Figure 14:
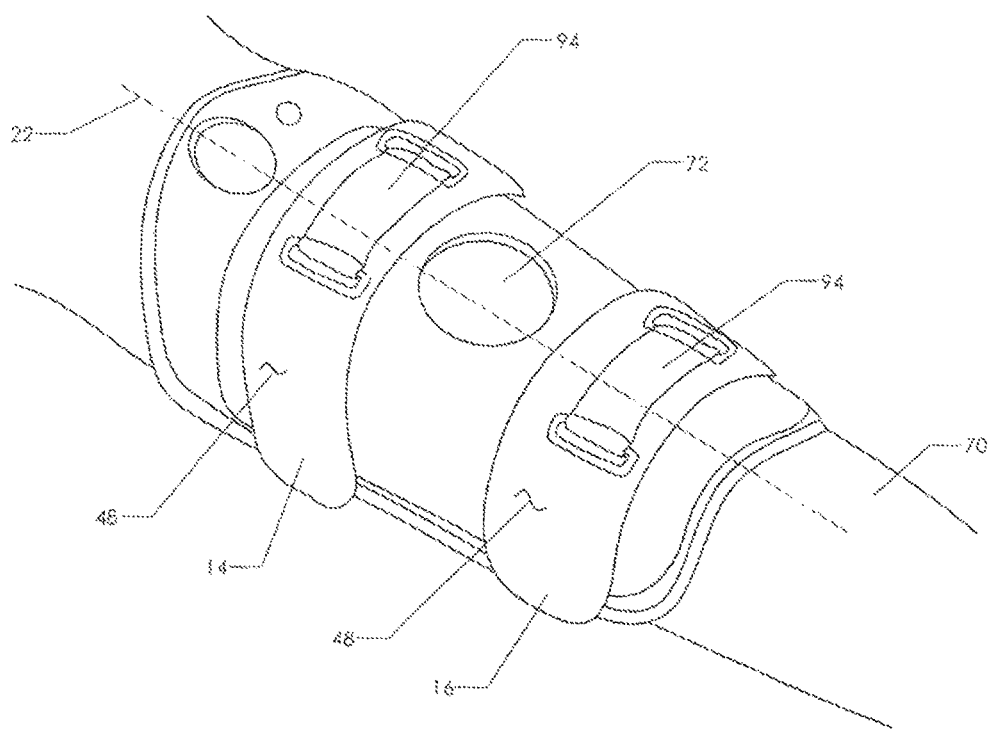
FIG. 14 is a perspective view, showing the brace of FIG. 11 with the two anchors of FIG. 13 installed.

FIG. 14 shows the two anchors 94 installed on the knee brace. One anchor is attached to top strap 14 by pressing the hook panel on the anchor against loop covering 48 on the top strap. A second anchor is attached to bottom strap 16 by pressing the hook panel on that second anchor against the loop covering on the bottom strap.

The two anchors may be placed anywhere on the outer facing surface of the knee brace. However, it is desirable to align the two anchors with anterior medial axis 22. Reinforced pad 76 is then placed against the posterior portion of the patient's knee. It is initially secured in position by pressing hook pad 90 (see FIG. 12) against the Loop covering on bottom strap 16 and pressing hook pad 92 against the loop covering on top strap 14.

Figure 15:
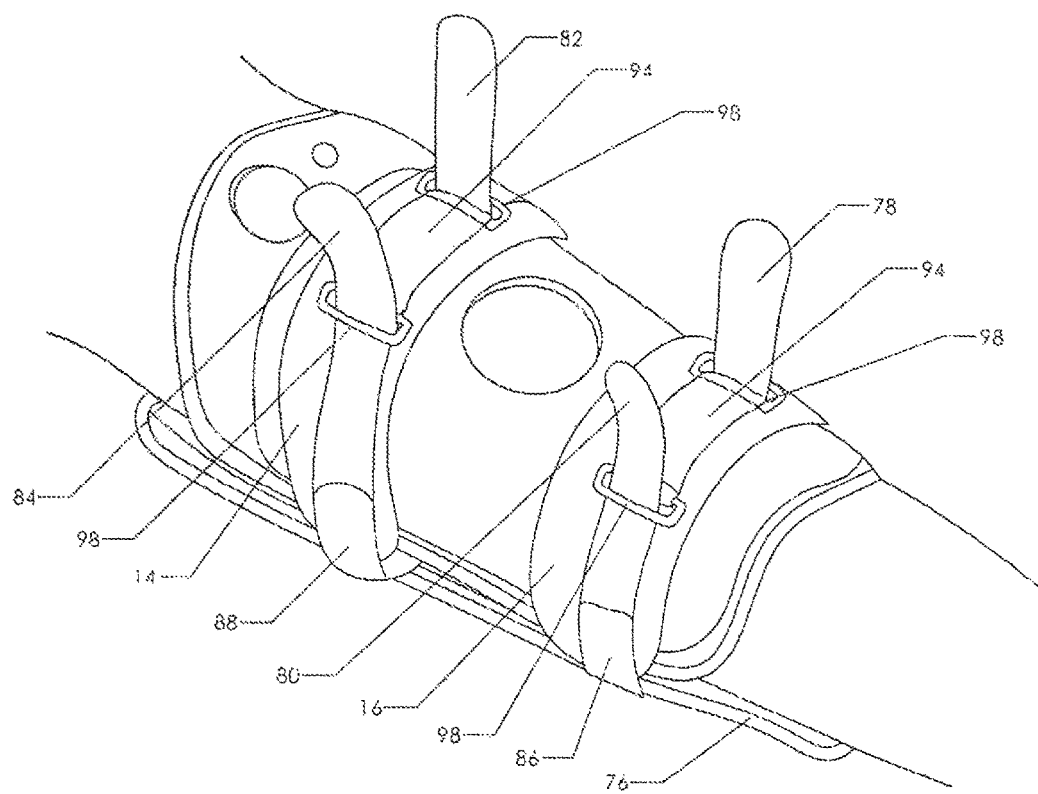
FIG. 15 is a perspective view, showing the installation of the removable anterior brace.

The four straps on the anterior brace are then threaded through the four loops 98 on the two anchors 94—as shown in FIG. 15. The four straps on the posterior brace are then drawn taut and each strap is folded back over its own hook panel. For example, the end of right lower pad strap 80 is pressed over hook pad 86.

It is preferable for the patient or a technician to simultaneously tighten and secure the two lower straps on the posterior brace and the two upper straps on the posterior brace. This maintains all the components in line with the anterior medial axis.

Figure 16:
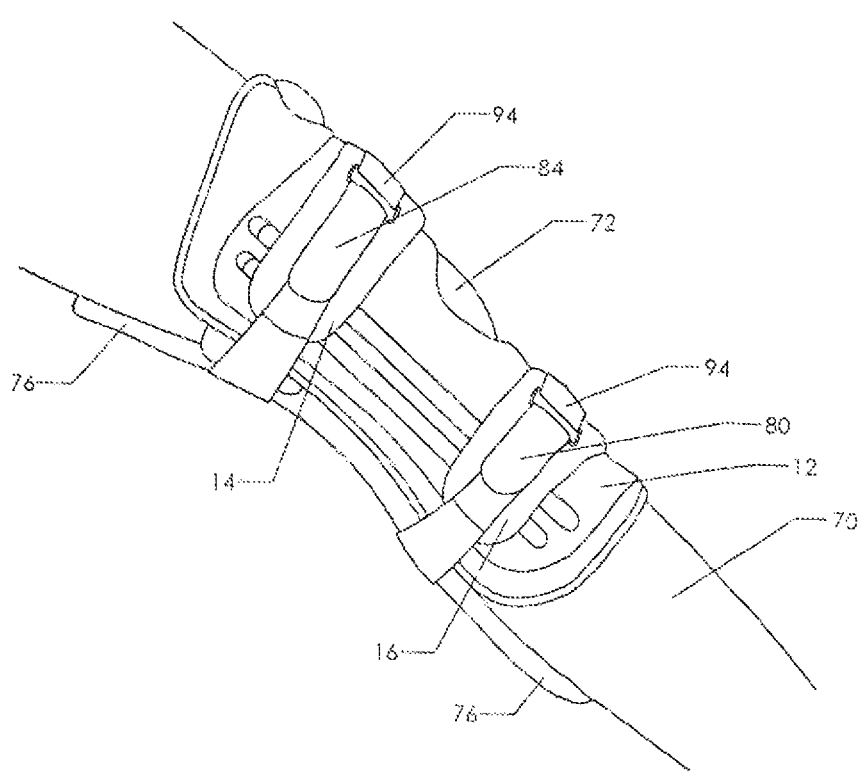
FIG. 16 is a side elevation view, showing the removable anterior brace in position.

FIG. 16 shows the completed assembly with reinforced pad 76 being held against the posterior portion of the knee. The straps connected to the posterior brace preferably lie over the straps attached to the wrap. The reader will observe for example that right upper pad strap 84 lies over top strap 14. Likewise, right lower pad strap lies over bottom strap 16.

The brace is ambidextrous, meaning that a single design will function for either a right knee or a left knee. The reader should also note that the arrangement of VELCRO hook and loop components may in all instances be reversed. In other words, a hook panel shown in the embodiments could just as easily be a loop panel (with the mating component being reversed as well).

Although the preceding descriptions present considerable detail they should be properly viewed as illustrating embodiments of the present invention rather than limiting the scope of the invention. Many more embodiments following the same principles will occur to those skilled n the art. Accordingly, the scope of the invention should be fixed by the following claims rather than by the examples given.

The invention claimed is:

1. A knee brace, comprising:
   a. a wrap, having an anterior medial axis, a right side, a left side, an inward facing surface, and an outward facing surface;
   b. a plurality of straps attached to said wrap, said straps configured to encircle a knee of a patient and attach said wrap thereto;
   c. said wrap including a selectively inflatable air bladder;
   d. at least one cold pack attached to said inward facing surface;
   e. a right lateral stay;
   f. a left lateral stay;
   g. said right and left lateral stays being removable;
   h. said wrap being changeable between a first configuration in which said right and left lateral stays are present and a second configuration in which said right and left lateral stays are absent;
   i. said first configuration restricting flexion of said knee and said second configuration allowing flexion of said knee;
   j. a separate posterior brace selectively attachable to said wrap, including,
      i. a pad stiffened by at least one stay,
      ii. a left lower pad strap configured to attach to said wrap,
      iii. a right lower pad strap configured to attach to said wrap,
      iv. a left upper pad strap configured to attach to said wrap, and
      v. a right upper pad strap configured to attach to said wrap.

2. The knee brace as recited in claim 1, wherein:
   a. said wrap includes an inner panel and an outer panel;
   b. said inflatable air bladder is located in between said inner panel and said outer panel; and
   c. said inner panel, said outer panel, and said air bladder are joined together by heat staking.

3. The knee brace as recited in claim 1, further comprising a hand pump for inflating said inflatable air bladder.

4. The knee brace as recited in claim 3, further comprising a release for selectively deflating said inflatable air bladder.

5. The knee brace as recited in claim 1, further comprising:
   a. a second right lateral stay;
   b. a second left lateral stay; and
   c. said second right and second left lateral stays being removable.

6. The knee brace as recited in claim 1, wherein:
   a. said inward facing surface of said wrap is covered in loop material; and
   b. said at least one cold pack includes at least one hook panel positioned to interface with said loop material on said inward facing surface.

7. The knee brace as recited in claim 1, wherein each of said plurality of straps includes a friction strip.

8. The knee brace as recited in claim 1, further comprising:
   a. said plurality of straps including a loop covering;
   b. a first anchor, having a first loop on a first end, and a second loop on a second end;
   c. said first anchor including a hook panel, with said first anchor being attached to said wrap by said hook panel on said first anchor engaging said loop covering on said plurality of straps;
   d. said first loop on said first anchor being configured to receive said left lower strap of said posterior brace; and
   e. said second loop on said first anchor being configured to receive said right lower strap of said posterior brace.

9. The knee brace as recited in claim 8, further comprising:
   a. a second anchor, having a first loop on a first end, and a second loop on a second end;
   b. said second anchor including a hook panel, with said second anchor being attached to said wrap by said hook panel on said second anchor engaging said loop covering on said plurality of straps;
   c. said first loop on said second anchor being configured to receive said left upper strap of said posterior brace; and
   d. said second loop on said second anchor being configured to receive said right upper strap of said posterior brace.

10. The knee brace as recited in claim 1, further comprising a knee relief.

11. A knee brace, comprising:
   a. a wrap, having an anterior medial axis, a right side, a left side, an inward facing surface, and an outward facing surface;
   b. a plurality of straps attached to said wrap, said straps configured to encircle a knee of a patient and attach said wrap thereto;
   c. said wrap including a selectively inflatable air bladder;
   d. at least one cold pack attached to said inward facing surface;
   e. said wrap being changeable between a first configuration in which said wrap restricts flexion of said knee and a second configuration in which said wrap allows flexion of said knee;
   f. a separate posterior brace selectively attachable to said wrap, including,
      i. a pad stiffened by at least one stay,
      ii. a left lower pad strap configured to attach to said wrap,
      iii. a right lower pad strap configured to attach to said wrap,
      iv. a left upper pad strap configured to attach to said wrap, and
      v. a right upper pad strap configured to attach to said wrap;
   g. a right lateral stay;
   h. a left lateral stay;
   i. said right and left lateral stays being removable; and j. said right and left lateral stays being present in said first configuration and absent in said second configuration.

12. The knee brace as recited in claim 11, further comprising:
   a. said plurality of straps including a loop covering;
   b. a first anchor, having a first loop on a first end, and a second loop on a second end;
   c. said first anchor including a hook panel, with said first anchor being attached to said wrap by said hook panel on said first anchor engaging said loop covering on said plurality of straps;
   d. said first loop on said first anchor being configured to receive said left lower strap of said posterior brace; and
   e. said second loop on said first anchor being configured to receive said right lower strap of said posterior brace.

13. The knee brace as recited in claim 12, further comprising:
   a. a second anchor, having a first loop on a first end, and a second loop on a second end;
   b. said second anchor including a hook panel, with said second anchor being attached to said wrap by said hook panel on said second anchor engaging said loop covering on said plurality of straps;
   c. said first loop on said second anchor being configured to receive said left upper strap of said posterior brace; and
   d. said second loop on said second anchor being configured to receive said right upper strap of said posterior brace.

* * * * *